United States Patent [19]

Kneller

[11] 4,066,743

[45] Jan. 3, 1978

[54] X-RAY CONTRAST AGENTS

[75] Inventor: Mills T. Kneller, University City, Mo.

[73] Assignee: Mallinckrodt, Inc., St. Louis, Mo.

[21] Appl. No.: 697,999

[22] Filed: June 21, 1976

[51] Int. Cl.$^2$ .................... C07D 263/14; A61K 29/02
[52] U.S. Cl. .................................... 424/5; 260/307 F; 260/518 A; 260/519
[58] Field of Search .................. 260/307 F; 424/5

[56] References Cited

U.S. PATENT DOCUMENTS

| 3,310,571 | 3/1967 | Lambert | 260/307 |
| 3,853,965 | 12/1974 | Ackerman | 260/516 |
| 3,917,631 | 11/1975 | Arlt | 260/307 F |

Primary Examiner—Raymond V. Rush
Attorney, Agent, or Firm—Koenig, Senniger, Powers and Leavitt

[57] ABSTRACT

3-Acetamido-5-(4,4-bishydroxymethyl-2-oxazolinyl)-2,4,6-triiodobenzoic acid, 3-acetamido-5-(4-methyl-4-hydroxymethyl-2-oxazolinyl)-2,4,6-triiodobenzoic acid, analogous compounds and salts and esters thereof are useful as X-ray contrast agents. The corresponding acyl halides are useful as intermediates.

12 Claims, No Drawings

X-RAY CONTRAST AGENTS

BACKGROUND OF THE INVENTION

This invention relates to the field of organic chemistry, and more particularly to novel triiodobenzoic acid derivatives useful as X-ray contrast agents.

Many 2,4,6-triiodobenzoic acid derivatives have been proposed for use as X-ray contrast agents. These include, among others as a subgroup, many 2,4,6-triiodoisophthalamic acid derivatives. Among the latter, certain N-hydroxyalkyl-2,4,6-triiodoisophthalamic acids have been disclosed. For example, both Guerbet et al. U.S. Pat. No. 3,622,616 and Salvesen et al. U.S. Pat. No. 3,702,866 disclose 5-acetamido-N-(2-hydroxyethyl)-2,4,6-triiodoisophthalamic acid. In addition, Salvesen et al. also disclose the compound N-(3-acetamido-5-carboxy-2,4,6-triiodobenzoyl)-N-methylglucamine, which may also be designated 5-acetamido-N-(D-gluco-1-deoxy-2,3,4,5,6-penta-hydroxyhexyl)-2,4,6-triiodo-N-methylisophthalamic acid.

Further, Almen et al. (U.S. Pat. No. 3,701,771) disclose a considerable number of non-ionic N-(2,4,6-triiodobenzoyl)-amines said to be useful as X-ray contrast agents in the cerebrospinal cavities, including one (compound 41) derived from tris(hydroxymethyl) aminomethane. This compound is designated as N-[3-N-methylacetamido-5-N-(beta-hydroxyethyl)-acetamido-2,4,6-triiodobenzoyl]N-[tris(hydroxymethyl)-methyl] amine. This compound was reported to have a rather low water solubility (0.86%) although many other compounds in the series were disclosed to be relatively highly soluble in water.

The use, as X-ray contrast media, of aqueous solutions of salts of various 2,4,6-triiodoisophthalamic and other 2,4,6-triiodobenzoic acids with pharmaceutically acceptable cations such as sodium, calcium and magnesium and alkanolamines such as ethanolamine, diethanolamine and meglumine (N-methylglucamine), is well known to those skilled in the art.

SUMMARY OF THE INVENTION

Among the objects of the invention may be mentioned the provision of new 2,4,6-triiodobenzoic acids and derivatives; the provision of compounds of the type indicated which are useful for the preparation of roentgenographic contrast media; and the provision of methods of preparing such compounds. Other objects and features will be in part apparent and in part pointed out hereinafter.

The present invention is directed to compounds of the formula:

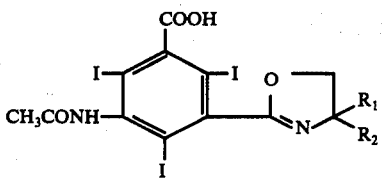

wherein $R_1$ is hydroxymethyl and $R_2$ is selected from the group consisting of hydroxymethyl and a lower alkyl group containing between 1 and 4 carbon atoms, and esters, salts and acyl halides thereof. The invention is also directed to a method of preparing such compounds by reducing a compound of the formula:

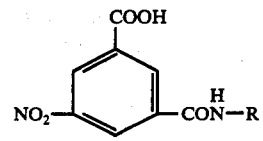

wherein R is selected from the group consisting of (trishydroxymethyl)-methyl and 2-(1,3-dihydroxy-2-lower alkyl)-propyl to form the corresponding amino compound, iodinating the latter to form the corresponding 2,4,6-triiodo compound, acylating the latter to form the corresponding acetamido compound, and dehydrating the latter to form a compound of the formula:

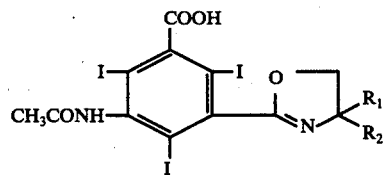

wherein $R_1$ is hydroxymethyl and $R_2$ is selected from the group consisting of hydroxymethyl and a lower alkyl group containing between 1 and 4 carbon atoms.

DESCRIPTION OF THE PREFERRED EMBODIMENTS

In accordance with the present invention, it has now been found that 3-acetamido-5-(4,4-bishydroxymethyl-2-oxazolinyl)-2,4,6-triiodobenzoic acid and 3-acetamido-5-(4-methyl-4-hydroxymethyl-2-oxazolinyl)-2,4,6-triiodobenzoic acid, analogous compounds and salts and esters thereof are useful as X-ray contrast agents. The invention is thus directed to compounds of the formula:

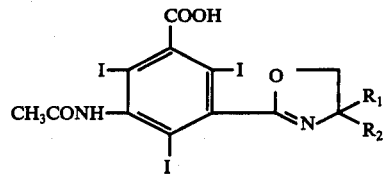

wherein $R_1$ is hydroxymethyl and $R_2$ is hydroxymethyl or a lower alkyl group containing between 1 and 4 carbon atoms, i.e., methyl, ethyl, propyl or butyl. The salts of these acids with pharmaceutically acceptable cations are useful in the preparation of X-ray contrast media intended primarily for intravenous pyelography. Other salts, such as ammonium salts, are useful as intermediates. Esters of the acids of the invention are useful in X-ray contrast media intended primarily for use in instillation procedures. Acyl halide derivatives of the acids are useful as intermediates for the preparation of amides and other non-ionic derivatives.

In the preparation of the acids of the invention, N[tris(hydroxymethyl)methyl]-5-nitroisophthalamic acid or 5-nitro-N[2-(1,3-dihydroxy-2-methyl)propyl]-isophthalamic, for example, is first reduced to form the corresponding amino compound. The amino compound is then iodinated to form the corresponding 2,4,6-triiodo-amino compound. The latter is then acylated to form the corresponding acetamido compound after which the latter is dehydrated to form 3-acetamido-5-(4,4-bishydroxymethyl-2-oxazolinyl)-2,4,6-triiodobenzoic acid or 3-acetamido-5-(4-methyl-4-hydroxymethyl-2-oxazolinyl)-2,4,6-triiodobenzoic acid. The oxazoline ring of these acids results from the dehydration of the (trishydroxymethyl) methyl carbamyl moiety or the 2-(1,3-dihydroxy-2-lower alkyl)-propyl carbamyl moiety, respectively.

3-Acetamido-5-(4,4-bishydroxymethyl-2-oxazolinyl)-2,4,6-triiodobenzoyl chloride, 3-acetamido-5-(4-methyl-4-hydroxymethyl-2-oxazolinyl)-2,4,6-triiodobenzoyl chloride or other acyl halides of the invention, all of which have suitable hydroxyl protecting groups, may be made by the following general method.

The acids of the invention which have the hydroxyl groups suitably protected may be treated with excess thionyl halide in N,N-dimethylacetamide. After removing the excess thionyl halide by evaporation under reduced pressure, the product is suitable for use as an intermediate in situ. Alternatively, the product is isolated by evaporating the solvent under vacuum.

The lower alkyl 3-acetamido-5-(4,4-bishydroxymethyl-2-oxazolinyl)-2,4,6-triiodobenzoates and 3-acetamido-5-(4-methyl-4-hydroxymethyl-2-oxazolinyl)-2,4,6-triiodobenzoates and other esters of the invention may be prepared by the following general method. For example, either a 3-acetamido-5-(4,4-bishydroxymethyl-2-oxazolinyl)-2,4,6-triiodobenzoyl chloride or a 3-acetamido-5-(4-methyl-4-hydroxymethyl-2-oxazolinyl)-2,4,6-triiodobenzoyl chloride with the hydroxyl groups thereof in a suitable protected form is treated with excess anhydrous lower alkanol in, for example, N,N-dimethylacetamide, in the presence of potassium carbonate. After the reaction is complete, the protecting groups are removed in a suitable manner, the reaction mixture is filtered to remove the inorganic salts and the lower alkyl 3-acetamido-5-(4,4-bishydroxymethyl-2-oxazolinyl)-2,4,6-triiodobenzoate or 3-acetamido-5-(4-methyl-4-hydroxymethyl-2-oxazolinyl)-2,4,6-triiodobenzoate is isolated by evaporating the excess alcohol and the solvent.

The following examples further illustrate the invention:

EXAMPLE 1

N[tris(hydroxymethyl)methyl]-5-nitroisophthalamic Acid

Methyl hydrogen 5-nitroisophthalate, 22.9 lbs. (46.0 g. moles—7% $H_2O$), was slurried in 8.8 gal. of water. Tris(hydroxymethyl)aminomethane (226.2 g. moles) 60.3 lbs. was added in two portions, 15 min. apart. The temperature dropped to 15° C. The slurry was warmed to a temperature of 43° C. to complete dissolution. The solution was cooled to 30°–32° C. and allowed to stand overnight (19 hrs.). At that time reaction was complete, as judged by thin-layer chromatography (TLC), using benzene:methylethylketone (MEK):88% formic acid (60:25:20) and isobutyl alcohol:isopropyl alcohol:$NH_4OH$ (100:40:50) systems. The solution was pumped into diluted sulfuric acid (1.52 gal. conc. $H_2SO_4$ + 3.59 gal. $H_2O$) in about 2–4 min. The temperature rose from 8° to 45° C. and crystallization began in 5–10 min. After stirring for 1 hour without cooling and 1 hour with cooling, the product was collected, reslurried in 7.2 gal. of ice water, collected again, and dried overnight at 60° C. Yield of crude product, 28.5 lbs., (92.4%), m.p. 173.5°–175.9° C. TLC using the systems described above showed some 5-nitroisophthalic acid impurity.

The product from above was dissolved in 520 lbs. of methanol at 55°–57° C. and the solution was concentrated until 378 lbs. of methanol remained. The solution was cooled, benzene (464 lbs.) was added, and the mixture was cooled overnight. The product was collected, reslurried in 10 gal. of methanol/benzene (1:3) and collected again. Yield 20.29 lbs., m.p. 175°–177° C.

The preparation was repeated on the same scale; a yield of 20.59 lbs. was obtained in the second run.

Both batches were combined (40.88 lbs.), dissolved in 41 gal. of 5% $NaHCO_3$ solution, the pH was adjusted to 5 with acetic acid and the solution was treated with 1.64 lbs. of charcoal at 25° C. The charcoal was filtered off and the filtrate was added to 9.3 gal. of 10% $H_2SO_4$ (w/v) and 8.4–9.0 gal. of $H_2O$. After one-fifth to one-fourth of the filtrate had been added to the $H_2SO_4$, precipitation started. The slurry was cooled 45 min. and the product was collected and washed with ice water. The product was reslurried in 15 gal. of ice water, collected, and dried at 65°–70° C. Yield, 34.5 lbs., m.p. 180.5°–181.9°.

The above product was recrystallized from water and dried at 65°–70° C. Yield 31.05 lbs. (48.6%); m.p. 184.9–185.9, N.E. found/theory 317.4/314.2. Only a trace impurity of 5-nitroisophthalic acid could be seen in the two TLC systems described above.

An analytical sample was further dried at 56° C./2 Torr. for 16 hours. Anal. Calcd. for $C_{12}H_{14}N_2O_8$: C, 45.88; H, 4.45; N, 8.91; N.E. 314.3. Found: C, 45.92; H, 4.56; N, 9.09; N.E. 314.1.

EXAMPLE 2

5-Amino-N[tris(hydroxymethyl)methyl]-isophthalamic Acid, Sodium Salt

5-Nitro-N-[tris(hydroxymethyl)methyl]-isophthalamic acid (314 g., 1.0 mole) was dissolved in water with the aid of NaOH, the pH was adjusted to 6.3–6.5, and the solution was treated with 2.67 g. of 5% Pd/C and 6.67 g. of charcoal for 35 minutes at 25°–30° C. The charcoal was removed, the solution was diluted to 1250 ml., and 6.5 g. of 5% Pd/C was added. Catalytic hydrogenation of the nitro group was carried out on a Parr shaker. Hydrogen uptake was quantitative in 4 hours, but shaking was continued overnight. The catalyst was removed, and the solution of 5-amino-N-[tris(hydroxymethyl)methyl]isophthalamic acid, sodium salt, was used promptly in the iodination step (Example 3) without isolation of the amine.

Alternatively, the hydrogenation may be carried out on a solution of the 5-nitro-[tris(hydroxymethyl)methyl]isophthalamic acid in methanol or other alcohol.

EXAMPLE 3

5-Amino-N-[tris(hydroxymethyl)methyl]-2,4,6-triiodoisophthalamic Acid

A solution of freshly prepared 5-amino-N[trish(hydroxymethyl)methyl]isophthalamic acid, sodium salt, (1.0 mole) in 1250 ml. of water (Example 2), was diluted to 3613 ml., and hydrochloric acid (187 ml.) was added. $NaICl_2$ (2.34N) was used as the iodinating agent. A total of 1410 ml. (10% excess) was added at 45° C. in three equal portions. The reaction mixture was stirred 15–20 minutes between additions. Progress of the iodination was followed by titration with thiosulfate. When the iodine uptake was 66% (about 2 hrs. at 45° C.) the temperature was slowly increased to 83° C. and the solution was diluted to twice its volume. After about 2–3 hrs.

more at 83°, the iodine uptake was 98.6%. The slurry was stirred overnight at 25° C. and the product was collected in the morning (iodine uptake was 100%), reslurried in 1 l. of water with a small amount of NaHSO₃ present, filtered, and dried. Yield, 524 g.

The crude product was recrystallized from 2.6 l. of ethanol. (Specially denatured alcohol, Formula 2B). Charcoal (35 g.) was used to decolorize the solution. The product crystallized from SD alcohol 2B in thick fluffy crystals. The solid was collected, reslurried in 800 ml. of SD alcohol 2B, collected, and air dried. It was then dissolved in 2 l. of water with NaOH, adjusted to pH 4.5 with acetic acid, and added to 1.1 l. of 5% HCl. The precipitate of 5-amino-N-[tris(hydroxymethyl)methyl]-2,4,6-triiodoisophthalamic acid was collected, reslurried in 700 ml. of water, collected again, and dried at 70° C. Yield, 362 g. (54.7%). Anal. Calcd. for $C_{12}H_{13}I_3N_2O_8$: C, 21.77; H, 1.96; I, 57.52; N, 4.23; N.E. 662.0. Found: C, 21.78; H, 2.25; I, 55.60; N, 4.03; N.E. 665.8.

The sodium salt of 5-amino-N-[tris(hydroxymethyl)-methyl]-2,4,6-triiodoisophthalamic acid has a water solubility of approximately 80% (w/v).

EXAMPLE 4

3-Acetamido-5-(4,4-bis(hydroxymethyl)-2-oxazolinyl)-2,4,6-triiodobenzoic Acid

5-Amino-N[tris(hydroxymethyl)methyl]-2,4,6-triiodoisophthalamic acid (81.8 g., 0.123 mole) was slurried in acetic anhydride (240 ml.) and concentrated sulfuric acid (16 ml.) was added in one portion at 18° C. with ice bath cooling. The reaction reached a temperature of 73° C. and the solids were mostly dissolved in 10 minutes. After stirring overnight the product was "watered out" with 1055 ml. of water to give a pink gum. Additional material was obtained by air evaporation of the liquors, followed by addition of ammonium hydroxide to pH 8-9 and evaporation to dryness with a rotating evaporator. The pink gum plus these residues were combined, dissolved in water (484 ml.) with ammonium hydroxide (325 ml.), and stirred at 63°-73° C. for 2 hours. Ammonia was bubbled in constantly during the 2 hour heating period. Water, ammonium hydroxide, and ammonium acetate were removed with a rotating evaporator at 80°-100° C./1-2 mm. The crude product was dissolved in water (264 ml.) and precipitated into 10% hydrochloric acid (264 ml.) at 25° C. A yield of 75.8 g. (90%) of crude product, which was mainly the desired product 3-acetamido-5-(4,4-bis(hydroxymethyl)-2-oxazolinyl)-2,4,6-triiodobenzoic acid but contained some of 5-acetamido-N-[tris(hydroxymethyl)-methyl]-2,4,6-triiodoisophthalamic acid (thin-layer chromatography system, benzene-methyl ethyl ketone-formic acid, 60:25:25). The material was dissolved in water (300 ml.) with sodium hydroxide and adjusted to pH 4-5, treated for 2 hours at 25° C. with charcoal (3 g.), and the filtrate was added to 10% hydrochloric acid (240 ml.) at 25° C. The product precipitated in 8 minutes (with seeding). After stirring the slurry for 15 minutes, the precipitate was collected, reslurried in water and air dried to yield 49.55 g. (58.3%). The thin-layer chromatogram (benzene-methyl ethyl ketone-formic acid, 60:25:25) showed mainly one spot but some of 5-acetamido-N[tris(hydroxymethyl)-methyl]-2,4,6-triiodoisophthalamic acid was present. The infrared and nuclear magnetic resonance spectra were consistent with the assigned structure. Anal. Calcd. for $C_{14}H_{13}I_3N_2O_6$: C, 24.51%; H, 1.91%; I, 55.50%; Found: C, 24.46%; H, 2.12%; I, 55.69%.

The melting point was 280.7°-283.2°° C. (dec.), and the solubility of the sodium salt was 95.8% (w/v). The N.E. was found/theory 682.2/686.0.

EXAMPLE 5

5-Nitro-N[2-(1,3-dihydroxy-2-methyl)propyl]-isophthalamic Acid

Methyl hydrogen 5-nitroisophthalate (169 g.; 0.75 mole) and 2-amino-2-methyl-1,3-propanediol (315 g.; 3.0 mole) were mixed in 450 ml. of $H_2O$. After brief warming (60°, 30 min.), a clear solution was obtained. The solution was allowed to stir at room temperature for 20 hrs., and was then poured slowly into a stirred solution of $H_2O$ (280 ml.) and $H_2SO_4$ (120 ml.) with cooling. The product precipitated. After cooling in an ice-bath for 1 hr., the product was collected, slurried in $H_2O$ (1200 ml.) and recollected. TLC indicated the product contained a small amount of 5-nitroisophthalic acid. The product was then treated with hot water (70°, 1500 ml.) and was collected when the water was still hot. This treatment yielded essentially pure 5-nitro-N-[2-(1,3-dihydroxy-2-methyl)propyl]-isophthalamic acid (167 g.; 0.56 mole; 74.7% yield). Spectral data (I.R. NMR, mass spectroscopy) confirmed the structure. This material is suitable for use in the following (hydrogenation) step.

Recrystallization from $H_2O$ (1:20 w/v) or from $H_2O/CH_3OH$ yielded a product melting at 184°-185° C.

EXAMPLE 6

5-Amino-N-[2-(1,3-dihydroxy-2-methyl)propyl]-2,4,6-triiodoisophthalamic Acid

5-Nitro-N-[2-(1,3-dihydroxy-2-methyl)-propyl]-isophthalamic acid (149.13 g.: 0.5 mole) was dissolved in dilute sodium hydroxide solution ($H_2O$ 400 ml.; 50% NaOH; 30 ml.). The solution was adjusted to pH 5.8 with acetic acid and was treated with charcoal (3.5 g.) and 5% Pd/C (1.4 g.). The solution was filtered, diluted to 625 ml. and 5% Pd/C (3.3 g.) was added. Hydrogenation was then carried out in a Parr shaker at room temperature. Hydrogen uptake was almost complete in about 3 hrs. although shaking was continued overnight. The solution was then filtered, the filtrate was diluted to 1810 ml. and hydrochloric acid (95 ml.) was added. A solution of 2.34 N sodium iododichloride ($NaICl_2$; 705 ml., 1.65 mole) was added in portions at 45° with stirring. One hour after the addition of $NaICl_2$ was finished, the solution was diluted to twice its volume and the reaction temperature was raised to 80°-83°. During the course of the reaction, the product gradually precipitated, and after reaction for 4 hrs. at this temperature, iodine uptake was 85% as determined by titration of an aliquot with standard sodium thiosulfate solution. At this point, $H_2O$ (1500 ml.) was added and the reaction (at 80°-83°) was allowed to continue for another 30 minutes. While the solution was still hot, the precipitated 5-amino-N-[2-(1,3-dihydroxy-2-methyl)-propyl]-2,4,6-triiodoisophthalamic acid was collected and dried (Yield, 234.5 g.). The filtrate, after standing at room temperature overnight, gave another crop of the product (17 g.). The total product weighed 251.5 g. (0.389 mole; 77.8% yield). TLC indicated the product was essentially pure. IR and NMR spectra were in agreement with the structure proposed. Anal. Calcd. C, 22.31; H, 2.03; I, 58.94; N, 4.34; N.E. 645.94. Found: C, 22.50; H, 2.46; I, 58.79; N, 4.27; N.E. 650.32.

The sodium salt of this acid is highly soluble in water (about 83% w/v).

EXAMPLE 7

5-Acetamido-N-[2-(1,3-dihydroxy-2-methyl)Propyl]-2,4,6-triiodoisophthalamic Acid A mixture of acetic anhydride (320 ml.) and $H_2SO_4$ (0.7 ml.) was warmed to 45° and 5-amino-N-[2-(1,3-dihydroxy-2-methyl)-propyl]-2,4,6-triiodoisophthalamic acid (64.6 g., 0.1 mole) was added in portions with stirring so that the reaction temperature was maintained at 50°-55°. After the addition of the compound, the reaction temperature was raised to 55°-60° and the reaction was continued for 1 hour. The resulting slurry was stirred overnight at room temperature and was then poured slowly into a mixture of $H_2O$ (600 ml.) and ice (300 g.). After the solution was stirred for 30 minutes, the resulting 5-acetamido-N-[2-(1,3-diacetoxy-2-methyl)-propyl]-2,4,6-triiodoisophthalamic acid was collected, slurried in $H_2O$ (800 ml.) and recollected. The compound was then dissolved in dilute ammonia solution ($H_2O$, 340 ml. and 29% ammonia solution, 310 ml.) and the solution was stirred and heated at 65°-70° for 2 hours to hydrolyze the acetate ester groups. The solution was cooled, filtered and poured slowly into an ice-cold mixture of $H_2O$ (500 ml.) and sulfuric acid (200 ml.). The 5-acetamido-N-[2-(1,3-dihydroxy-2-methyl)-propyl]-2,4,6-triiodoisophthalamic acid precipitated, and was collected, slurried in $H_2O$ (100 ml.) and recollected (47.4 g.; 0.069 mole; 69% yield). TLC, one spot. IR and NMR spectroscopy confirmed the structure. MP 270°-272° C. (decomp.). Anal. Calcd. $C_{14}H_{15}I_3N_2O_6$: C, 24.43; H, 2.20; I, 55.34; N, 4.07; N.E. 688.0. Found: C, 24.36; H, 2.28; I, 55.21; N, 4.06; N.E. 684.4.

EXAMPLE 8

3-Acetamido-5-(4-methyl-4-hydroxymethyl-2-oxazolinyl)-2,4,6-triiodobenzoic Acid

5-Acetamido-N-[2-(1,3-dihydroxy-2-methyl)-propyl]-2,4,6-triiodoisophthalamic acid (96 g.) was slurried in acetic anhydride (250 ml.) and sulfuric acid (30 ml.) was slowly added so as to maintain a gradual rise in the temperature of the reaction. The temperature reached 70° C. and after about 5 minutes it slowly dropped. The reaction was stirred for 3 hours and water was added slowly. No cooling was used and the temperature of the reaction mixture reached 110° C. for about 8 minutes and then began to drop. The reaction mixture was then treated with ammonium hydroxide (250 ml.) and gaseous ammonia and warmed at 75°-78° C. for 3 hours and after stirring overnight the reaction mixture was acidified with concentrated hydrochloric acid as a crystalline product came out. The solids were collected, washed with water and dissolved in 10% sodium hydroxide. The pH was adjusted with acetic acid to 5 and charcoal was added. After stirring 1 hour, the solution was filtered and the product crystallized upon the addition of concentrated hydrochloric acid to give material which was washed with acetone slurries twice, yield 50.82 G. The thin-layer chromatogram of this product indicated that about 2-3% of 5-acetamido-N-[2-(1,3-dihydroxy-2-methyl)-propyl]-2,4,6-triiodoisophthalamic acid and about 1% of an unknown remained as impurities. The material, 48 g., was slurried in water (1 l.), dissolved with ammonium hydroxide, filtered to remove impurities and acidified with concentrated hydrochloric acid to pH 1. The product was collected and air-dried, reslurried twice with ethyl acetate, dried and examined by thin-layer chromatography. About 1% 5-acetamido-N-[2-(1,3-dihydroxy-2-methyl)-propyl]-2,4,6-triiodoisophthalamic acid remained as an impurity (isobutyl alcohol-isopropyl alcohol-ammonium hydroxide, 100:40:40). A small amount of high $R_f$ impurity was also present. 5-Acetamido-N-[2-(1,3-dihydroxy-2-methyl)-propyl]-2,4,6-triiodoisophthalamic acid and another impurity could also be seen in the benzene-methyl ethyl ketone-formic acid (90:37.5:30) thin-layer chromatography system. Anal. Calcd. for $C_{14}H_{13}I_3N_2O_5$: C, 25.10; H, 1.96; I, 56.82; N, 4.18. Found: C, 25.06; H, 1.88; I, 57.03; N, 4.08.

The melting point was 283°-285° C. (dec.). The solubility of the sodium salt was 73.85%.

Toxicity evaluations by three different techniques were carried out on solutions of the N-methylglucamine salts of 3-acetamido-5-(4,4-bishydroxymethyl-2-oxazolinyl)-2,4,6-triiodobenzoic acid and 3-acetamido-5-(4-methyl-4-hydroxymethyl-2-oxazolinyl)-2,4,6-triiodobenzoic acid. The techniques utilized are outlined below.

I. Acute Intravenous Toxicity Studies in Mice

Swiss Albino mice (Charles River) were dosed in the lateral tail vein with solutions of the iodinated compounds containing 50.4% iodine in the case of 3-acetamido-5-(4,4-bishydroxymethyl-2-oxazolinyl)-2,4,6-triiodobenzoic acid and 28.2% iodine in the case of 3-acetamido-5-(4-methyl-4-hydroxymethyl-2-oxazolinyl)-2,4,6-triiodobenzoic acid, injected at the rate of 1 ml./min. Following injections the animals were observed for immediate reactions and then daily throughout a seven day observation period. The $LD_{50}$ values were calculated by the method of Litchfield and Wilcoxon (J. of Pharmac. and Exptl. Therap. 96:99–113, 1949).

II. Intracerebral Toxicity in Mice

Swiss Albino mice (Charles River) were used. Fixed volumes of solutions of various concentrations of the iodinated compounds were injected intracerebrally via a 27 gauge needle, (¼ inch length) according to the method of Haley, et al. (Br. J. of Pharmac. 12:12–15, 1957). The animals were observed immediately after injections and daily throughout a 7 day observation period. The $LD_{50}$ values were calculated by the method of Litchfield and Wilcoxon (J. of Pharmac. and Exptl. Therap. 96:99–113, (1949)).

III. Intracisternal Toxicity in Rats

Sprague Dawley (Carworth) rats were used. The method used was a variation of the procedure outlined by Melartin et al. (Invest. Rad. 5:13–21, 1970). After dosing, the animals were housed individually, and observed for immediate reactions and periodically for a 2 day observation period. The $LD_{50}$ values were calculated according to the method of Litchfield and Wilcoxon, (J. of Pharmac. and Exptl. Therap. 96:99–115, 1949).

The results of the toxicity evaluations are set forth in Table 1.

Table 1

Toxicity Values for N-Methylglucamine Salts of 3-Acetamido-5-(4,4-bishydroxymethyl-2-oxzolinyl-2,4,6-Triiodobenzoic Acid and 3-Acetamido-5-(4-methyl-4-hydroxymethyl-2-oxazolinyl)-2,4,6-Triiodobenzoic Acid

| Compound | LD$_{50}$ of Meglumine Salt* | | |
|---|---|---|---|
| | I.V. (Mice) | Intra-cerebral (Mice) | Intra-cisternal (Rats) |
| 3-Acetamido-5-(4,4-bishydroxymethyl-2-oxazolinyl)-2,4,6-Triiodobenzoic Acid | 5,522 | 485 | 55 |
| 3-Acetamido-5-(4-methyl-4-hydroxymethyl-2-oxazolinyl-2,4,6-Triiodobenzoic Acid | 5,500 | 280 | 28 |

*All LD$_{50}$ values are expressed in terms of mg. contained iodine/kg. animal body weight.

The LD$_{50}$ values for the N-methylglucamine salts of the compounds of the invention suggest that these and other non-toxic water salts of these acids would be useful X-ray contrast agents for intravenous pyelography and other radiographic procedures.

In view of the above, it will be seen that the several objects of the invention are achieved and other advantageous results attained.

As various changes could be made in the above products and methods without departing from the scope of the invention, it is intended that all matter contained in the above description shall be interpreted as illustrative and not in a limiting sense.

What is claimed is:

1. A compound of the formula:

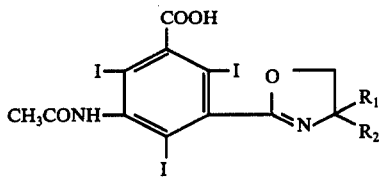

wherein R$_1$ is hydroxymethyl and R$_2$ is selected from the group consisting of hydroxymethyl and a lower alkyl group containing between 1 and 4 carbon atoms, and esters thereof with lower alkanols, salts thereof with pharmaceutically acceptable cations, and acyl halides thereof.

2. A compound as defined in claim 1 which is 3-acetamido-5-(4,4-bishydroxymethyl-2-oxazolinyl)-2,4,6-triiodobenzoic acid.

3. A compound as defined in claim 1 which is a salt of 3-acetamido-5-(4,4-bishydroxymethyl-2-oxazolinyl)-2,4,6-triiodobenzoic acid with a pharmaceutically acceptable cation.

4. A compound as defined in claim 3 wherein the pharmaceutically acceptable cation is sodium.

5. A compound as defined in claim 3 wherein the pharmaceutically acceptable cation is N-methylglucamine.

6. A compound as defined in claim 1 which is 3-acetamido-5-(4-methyl-4-hydroxymethyl-2-oxazolinyl)-2,4,6-triiodobenzoic acid.

7. A compound as defined in claim 1 which is a salt of 3-acetamido-5-(4-methyl-4-hydroxymethyloxazolinyl)-2,4,6-triiodobenzoic acid with a pharmaceutically acceptable cation.

8. A compound as defined in claim 7 wherein the pharmaceutically acceptable cation is sodium.

9. A compound as defined in claim 7 wherein the pharmaceutically acceptable cation is N-methylglucamine.

10. An X-ray contrast medium comprising an aqueous solution of a salt of a compound selected from the group consisting of 3-acetamido-5-(4,4-bishydroxymethyl-2-oxazolinyl)-2,4,6-triiodobenzoic acid and 3-acetamido-5-(4-methyl-4-hydroxymethyl-2-oxazolinyl)-2,4,6-triiodobenzoic acid with at least one pharmaceutically acceptable cation.

11. An X-ray contrast medium as defined by claim 10 wherein said compound is 3-acetamido-5-(4,4-bishydroxymethyl-2-oxazolinyl)-2,4,6-triiodobenzoic acid.

12. An X-ray contrast medium as defined by claim 10 wherein said compound is 3-acetamido-5-(4-methyl-4-hydroxymethyl-2-oxazolinyl)-2,4,6-triiodobenzoic acid.

* * * * *